United States Patent [19]
Smeets et al.

[11] Patent Number: 5,607,422
[45] Date of Patent: Mar. 4, 1997

[54] CATHETER WITH ELONGATED SIDE ELECTRODE

[75] Inventors: Joseph L. R. M. Smeets, Gronsveld; Wilhelmus P. M. M. Van Erp, Leek, both of Netherlands

[73] Assignee: Cordis Corporation, Miami Lakes, Fla.

[21] Appl. No.: 269,000

[22] Filed: Jun. 30, 1994

[30] Foreign Application Priority Data

May 7, 1993 [NL] Netherlands ............................ 9301182

[51] Int. Cl.⁶ .............................. A61B 17/39; A61N 1/05
[52] U.S. Cl. ................. 606/41; 606/49; 607/99; 607/122; 128/642
[58] Field of Search ............................ 128/642; 607/122, 607/98, 99; 606/48, 49, 50, 41

[56] References Cited

U.S. PATENT DOCUMENTS

| | | | |
|---|---|---|---|
| 4,945,912 | 8/1990 | Langberg | 128/642 |
| 5,334,193 | 8/1994 | Nardelle | 606/41 |
| 5,429,130 | 7/1995 | Goldman | 128/642 |
| 5,462,545 | 10/1995 | Wang et al. | 606/41 |

FOREIGN PATENT DOCUMENTS

| | | | |
|---|---|---|---|
| 0394446 | 10/1988 | European Pat. Off. | |
| 9007303 | 7/1990 | WIPO | 606/50 |
| WO92/02272 | 2/1992 | WIPO | |
| WO93/08869 | 5/1993 | WIPO | |

*Primary Examiner*—Lee S. Cohen
*Attorney, Agent, or Firm*—Gerstman, Ellis & McMillin, Ltd.

[57] ABSTRACT

The invention relates to a catheter comprising a tubular body with a distal end. A proximal catheter end is provided with a connector. A flexible catheter section is defined at the distal end. The wall of the flexible section comprises an elongated, flexible heating element extending in the longitudinal direction of the catheter, wherein at least one electric conductor for the heating element extends from the heating element to adjacent the proximal end. The heating element is preferably an element which can be exited by high frequency electromagnetic oscillations.

8 Claims, 2 Drawing Sheets

CATHETER WITH ELONGATED SIDE ELECTRODE

BACKGROUND OF THE INVENTION

The invention relates to a catheter designed to be advanced in a usual manner via the vascular system of the patient into the heart for the purpose of investigation or treatment.

DESCRIPTION OF THE INVENTION

The catheter according to the invention comprises a tubular body with a distal end having a flexible, tubular end section, and a proximal end provided with a connector. The wall of the flexible end section comprises an elongated heating element extending in the longitudinal direction of the catheter, and wherein at least one electric conductor connected to the heating element extends from the heating element through the catheter body to a position close to the proximal end. The heating element is preferably a flexible strip (or a wire).

The catheter according to the invention is especially designed to be used when treating certain cardiac arrhythmias. For this purpose, the distal end section of the catheter with the strip-shaped heating element is placed against the wall of the heart. The heating element is then excited, thus heating and disturbing the tissue in contact with the strip-shaped element. Consequently any conduction along the surface of the heart will be interrupted. By this invention, a smaller, longer, more precise area of the heart can be inactivated when compared with solid-end electrode catheters of the prior art.

It has become apparent that certain types of tachycardias can be caused by different activation waves in the cardiac tissue. Treatment with the catheter according to the invention as described will block the conduction of these waves, and consequently the arrhythmia can be cured.

Atrial fibrillation and flutter can be treated by creating a conduction block in the free wall of the atrium with the aid of the heating element. The anomalous conduction pathways are thus destroyed but the normal pathways remain intact because of the narrow dimension of the strip-shaped element used herein.

With the catheter according to the invention also the so called re-entry pathways, situated between the coronary sinus and the tricuspid valve, can be treated. With the known treatments the exact location of this re-entry pathway must be determined carefully, and subsequently destroyed. With the elongated electrode situated at the flexible part of the catheter according to the invention, the area can be ablated in its entirety in one treatment at a single catheter position.

In general it is very difficult to treat cardiac arrhythmias following a myocardial infarction. Expectations are that also these tachycardias and the like can be treated successfully using the catheter according to the invention.

DESCRIPTION OF THE DRAWINGS

The invention will be explained in greater detail with reference to the attached drawings.

DESCRIPTION OF A PREFERRED EMBODIMENT

Figure 1:
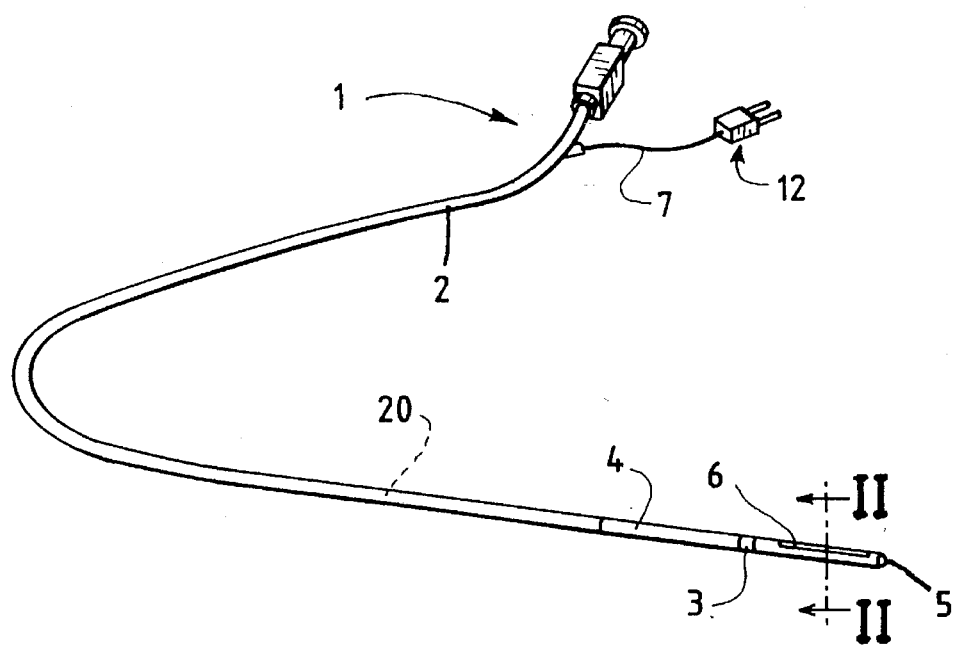
FIG. 1 shows a perspective view of a catheter according to the invention.
Figure 2:
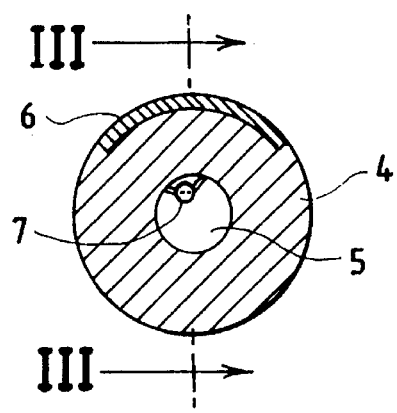
FIG. 2 represents an enlarged cross-section of the catheter of FIG. 1, at II—II in FIG. 1.
Figure 3:
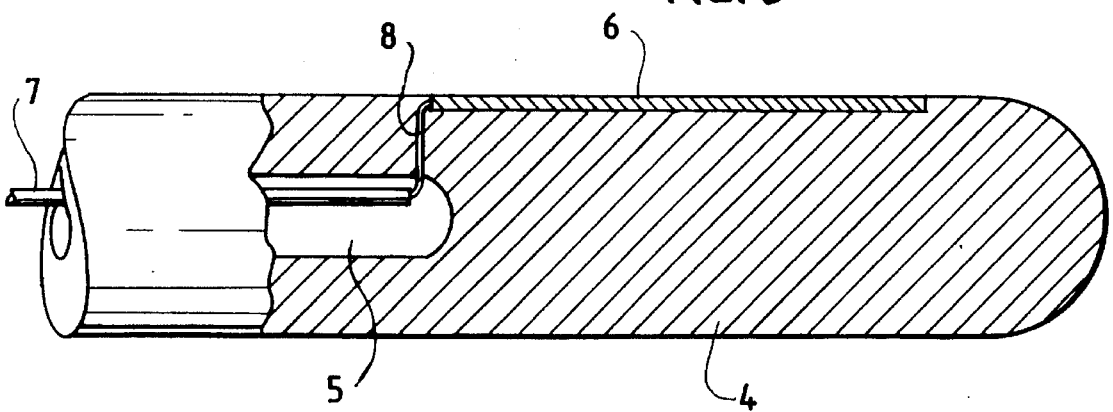
FIG. 3 shows a longitudinal cross-section of the catheter at III—III in FIG. 2.

The catheter 1 as shown in FIG. 1, comprises in the usual manner a tubular body 2 with a distal end section 4, to be introduced into the patient, and a proximal end provided with connectors 12.

The distal end section 4 can be more flexible than the rest of the catheter body 2, being manufactured of a material different from that of the body 2 or because its structure is different. In particular the end section 4 can be more pliable, as a tubular reinforcing layer of braided metal wire is lacking, while such a conventional braided reinforcement 20 is present in body 2, in order to provide it with sufficient compression resistance and stiffness, plus torsional stiffness.

The wall of the flexible end section 4 is provided with a strip-shaped heating element 6 extending in the longitudinal direction of the catheter. With the illustrated embodiment, this heating element is made up of a thin metal strip made of a conventional alloy, embedded in the wall of the end-section 4. Strip 6 may also be made of a conductive plastic or elastomer. Connected to the heating element 6 is a conductor 8 in the form of an electric wire, extending through catheter lumen 5 into contact with strip 6 close to the distal end of catheter 1. The conductor 8 is sheathed in insulation 7, and extends toward the catheter proximal end, to emerge close to the proximal end of catheter 1. The conductor 8 is connected to a connector plug 12 to which a suitable electric current can be supplied in a controlled manner. Preferably this will be a high frequency current with a frequency of, for example, 550 kHz. During the treatment the current will flow through the patient's body to a ground plate beneath the patient.

Figure 4:
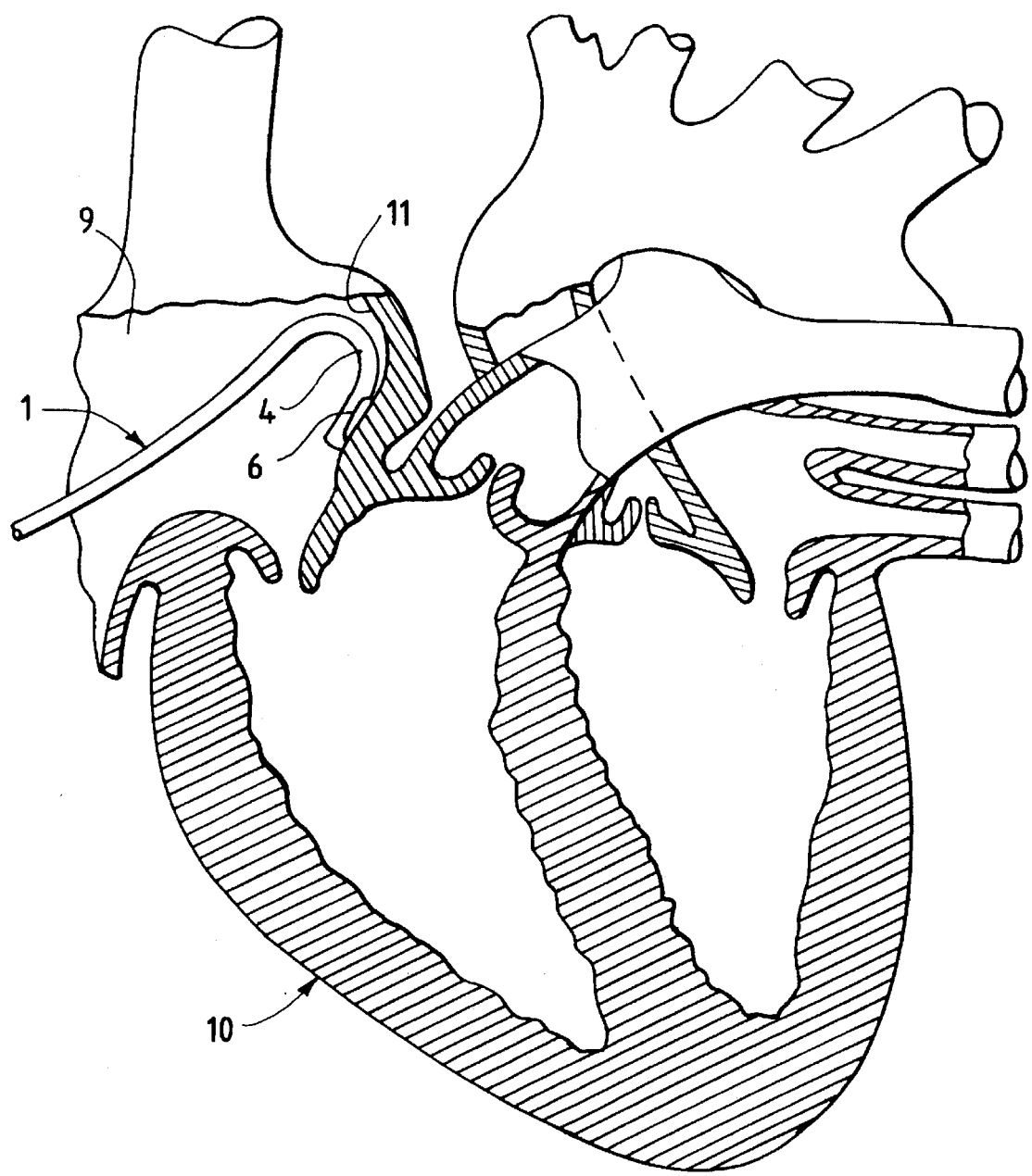
FIG. 4 illustrates the application of the catheter according to the invention.

The catheter 1 according to the invention is usually introduced into the venous system in the groin and advanced into the right atrium 9 of the heart 10 of the patient. By careful manipulation of the catheter 1, the heating element 6 will be placed firmly against the wall 11 of the atrium 9. As the end section 4 and heating element 6 of the catheter 1 is flexible, the heating element 6 can be manoeuvred over its entire length against the wall 11 (FIG. 4) for achieving a precisely desired positioning.

The area surrounding the end-section 4 of the catheter 1 can be made visible in the usual manner in a catheterization laboratory by using x-rays.

When a high frequency electric current as described above is used, the same catheter is preferably not used for the injection of contrast medium.

As soon as the heating element 6 is positioned correctly, an electric current is applied, as a result of which the heating element 6 will coagulate adjacent tissue. Due to this coagulation, a conduction block is created, terminating the cardiac arrhythmia. The catheter can be manipulated in such a fashion that the heating strip 6 can be positioned against the wall 11 in several places to effect the required superficial disturbance of the tissue. Also heating strip 6, while narrow as a wire, may be of any desired length to provide treatment along a line.

With the catheter 1 according to the invention as illustrated in FIG. 1, an electrode, in this example a ring-shaped electrode 3, has been incorporated proximally of the heating element 6. A conductor connected to this electrode 3 runs also to the proximal end. Consequently the catheter can also be used as a so-called mapping catheter.

The heating element can also be replaced with a "window", whereby a laser beam will be transported through optical fibers in the catheter, to be aimed directly at that section of the wall of the heart which is to be ablated.

A suitable application of the embodiment using high frequency electrical current is achieved with a catheter of which the basic body 2 of the type described has an embedded tubular, braided reinforcing layer of metal wire 20, which is absent from distal section 4. This metal reinforcing layer is electrically connected with the zero potential, i.e., is grounded, so that it functions as a shield, and no unwanted effects of leaking electromagnetic energy can occur.

The realization of the different embodiments of catheters according to the invention mentioned above are within the reach of a professional, and therefore do not need to be explained or described in greater detail. The claims encompass all possible versions of embodiments of catheters with a strip or wire-shaped heating element, along with those which have not been mentioned specifically above.

That which is claimed is:

1. A catheter and power source comprising a tubular body extending in a longitudinal direction and having a distal end and a proximal end, the distal end having a flexible, tubular end section having a wall, said wall carrying an elongated, flexible electric heating element extending in the longitudinal direction of the catheter and on one side only of the catheter, said heating element being substantially exposed to the exterior of said catheter to permit transfer of electric current from the heating element to surrounding tissue, said heating element being electrically connected to a power source for heating by high frequency electromagnetic oscillations, and a conductor connected to the heating element extending from the element through the tubular body to said power source adjacent the proximal end.

2. The catheter as claimed in claim 1, wherein the tubular body is of the type which has an embedded reinforcing tubular layer of metal wire braid, and a connection for said braid to ground.

3. The catheter of claim 1 in which said heating element is a strip or wire.

4. The catheter of claim 1 in which said wall carries only a single, elongated, flexible, electric heating element.

5. A catheter comprising a tubular body extending in a longitudinal direction and having a distal end and a proximal end, the distal end having a flexible tubular end section having a wall, said wall carrying an elongated, flexible electric heating strip or wire extending in the longitudinal direction of the catheter on only one side thereof, said strip or wire being substantially exposed to the exterior of said catheter to permit electric current flow between the strip or wire and tissue surrounding the catheter, and a conductor connected to the heating strip or wire and extending through the tubular body to a position adjacent the proximal end, said heating strip or wire being excitable for heating by high frequency electromagnetic oscillations, said tubular body being of the type which has an embedded reinforcing tubular layer of metal wire braid surrounding said conductor, and a connection for said metal braid to ground.

6. The catheter as claimed in claim 5 in which said wall carries only a single, elongated, flexible, electric heating strip or wire.

7. The method of medical treatment which comprises inserting a catheter into a patient, said catheter comprising a tubular body extending in a longitudinal direction and having a distal end and a proximal end, said distal end having a flexible, tubular end section having a wall, said wall carrying an elongated, flexible electric heating element extending in the longitudinal direction of the catheter and on only one side of said catheter, said heating element being exposed to the exterior of said catheter; bringing said flexible electric heating element into complete contact without spacing with tissue desired to be destroyed, and providing an electric current that passes between said heating element and said tissue to destroy said tissue.

8. The method of claim 7 in which said electric current comprises high frequency electromagnetic oscillations.

\* \* \* \* \*